United States Patent
Safreno

(10) Patent No.: US 9,943,049 B2
(45) Date of Patent: Apr. 17, 2018

(54) VISION-BASED POLLINATION SYSTEM

(71) Applicant: Dina Safreno, Woodside, CA (US)

(72) Inventor: Dina Safreno, Woodside, CA (US)

(*) Notice: Subject to any disclaimer, the term of this patent is extended or adjusted under 35 U.S.C. 154(b) by 231 days.

(21) Appl. No.: 14/825,131

(22) Filed: Aug. 12, 2015

(65) Prior Publication Data
US 2017/0042102 A1    Feb. 16, 2017

(51) Int. Cl.
*A01H 1/02* (2006.01)

(52) U.S. Cl.
CPC ................................ *A01H 1/025* (2013.01)

(58) Field of Classification Search
CPC ... A01G 7/00; A01G 7/06; A01H 1/00; A01H 1/02; A01H 1/025; A01M 7/0071
USPC ............... 47/58.1 R, 58.1 FV, 1.41; 382/110
See application file for complete search history.

(56) References Cited

U.S. PATENT DOCUMENTS

| | | | | |
|---|---|---|---|---|
| 2,570,511 A * | 10/1951 | Blair | ...................... | A01H 1/025 102/531 |
| 2,685,149 A * | 8/1954 | Hvistendahl | ........... | A01H 1/025 172/29 |
| 3,514,038 A * | 5/1970 | McQuinn | ............ | A01M 7/0071 239/165 |
| 3,728,817 A * | 4/1973 | Huey | ...................... | A01H 1/025 47/1.41 |
| 3,774,845 A * | 11/1973 | Folkert | ............... | A01M 7/0014 239/78 |
| 4,087,937 A * | 5/1978 | Meader | .................. | A01H 1/025 47/1.41 |
| 4,644,683 A * | 2/1987 | Jones | ..................... | A01H 1/025 244/136 |
| 6,141,904 A | 11/2000 | Greaves | | |
| 6,671,582 B1 * | 12/2003 | Hanley | .................. | A01B 51/02 250/339.11 |
| 6,760,654 B2 * | 7/2004 | Beck | .................... | A01B 79/005 342/357.31 |
| 2013/0118066 A1 | 5/2013 | Cope | | |
| 2013/0118067 A1 * | 5/2013 | Cope | ........................ | A01G 7/00 47/1.41 |

(Continued)

FOREIGN PATENT DOCUMENTS

| JP | 2008064681 | 3/2008 |
|---|---|---|
| JP | 2011200196 | 10/2011 |
| JP | 2013150584 | 8/2013 |

(Continued)

*Primary Examiner* — Trinh T Nguyen
(74) *Attorney, Agent, or Firm* — Fitch, Even, Tabin & Flannery LLP

(57) ABSTRACT

Methods and apparatus for a vision-based pollination system. The vision-based pollination system includes a mobile support apparatus configured to traverse a crop field. The mobile support apparatus supports a pollination liquid storage tank fluidly coupled to a plurality of pollen applicators. The apparatus includes pollination nodes including a vision system and a camera. Each pollination node is coupled to and controls a portion of the pollen applicators. In operation, the mobile support apparatus traverses the crop field, each pollination node repeatedly taking photographs of a portion of the crop field, identifying locations for delivering the pollination liquid, and determining when to operate the pollen applicators to deliver the pollination liquid to the identified locations as the vision-based pollination system traverses the crop field.

22 Claims, 8 Drawing Sheets

(56) References Cited

U.S. PATENT DOCUMENTS

2016/0260207 A1* 9/2016 Fryshman ............. G06T 7/0008

FOREIGN PATENT DOCUMENTS

| JP | 2013158288 | 8/2013 |
|----|------------|--------|
| JP | 2013226161 | 11/2013 |
| WO | 2014085774 | 6/2014 |

* cited by examiner

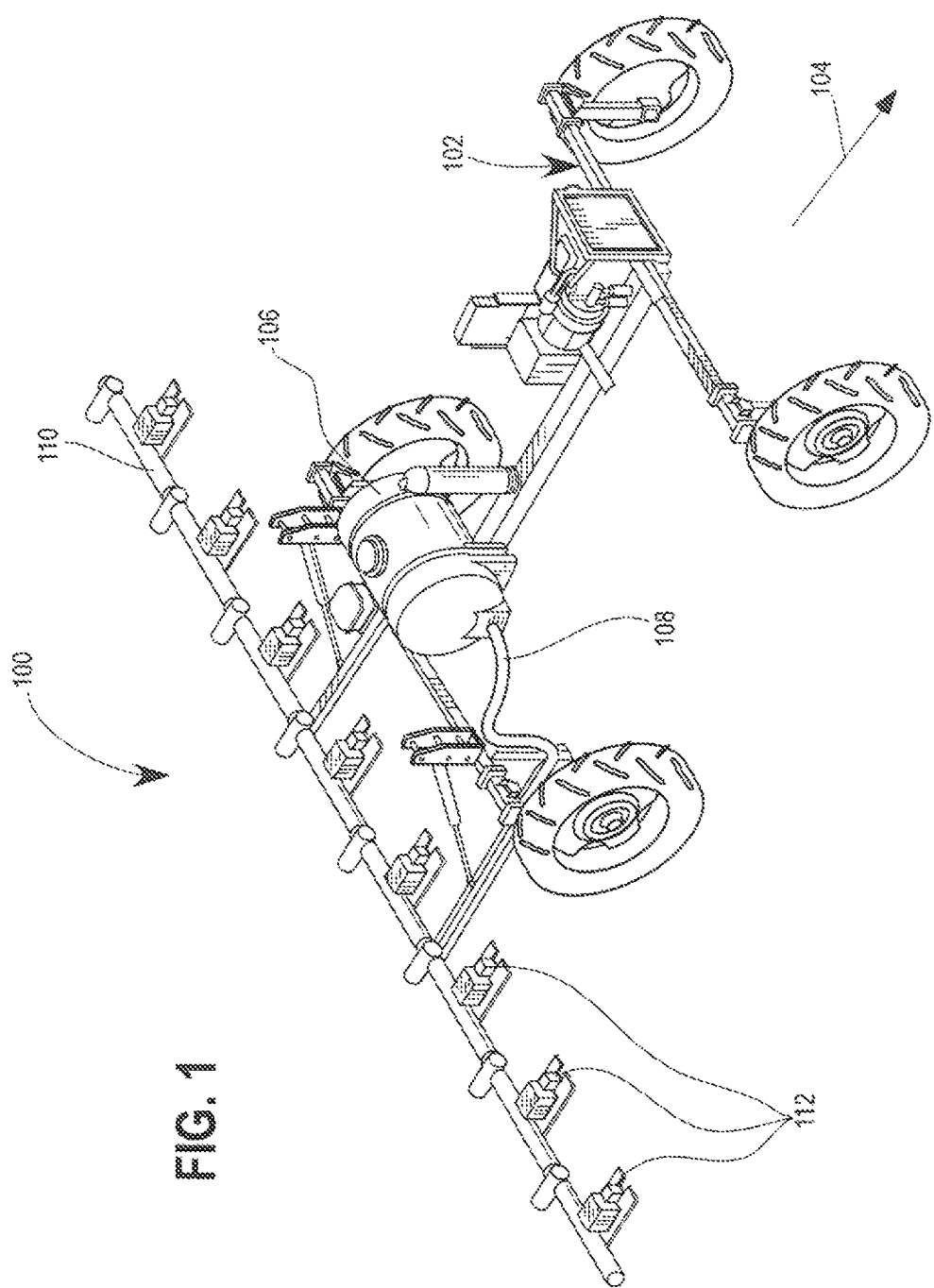

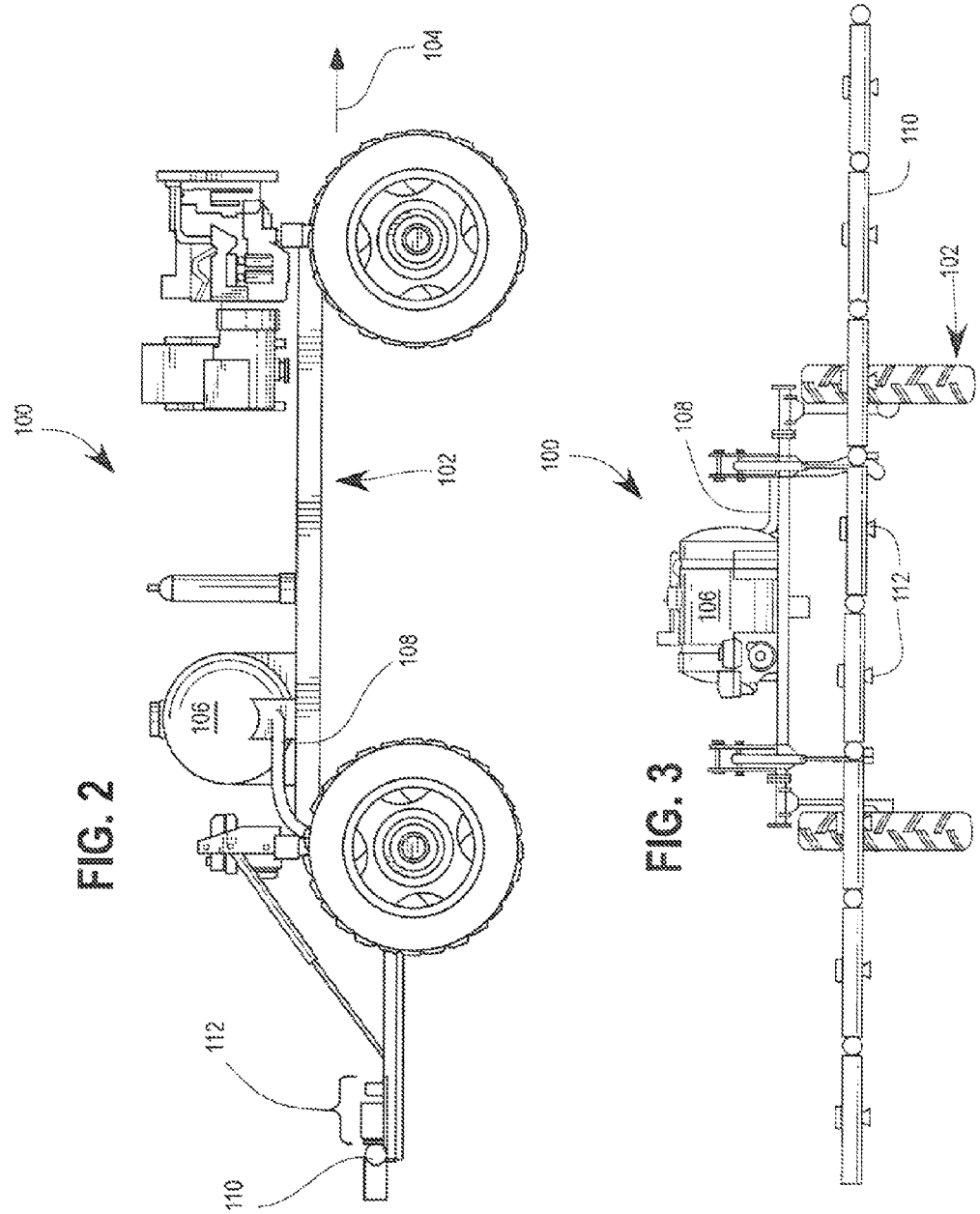

VISION-BASED POLLINATION SYSTEM

BACKGROUND OF THE INVENTION

1. Field of the Invention

The present invention relates generally to systems and methods for pollination, and more specifically to systems and methods for automated pollination. Even more specifically, the present invention relates to systems and methods for automated pollination including vision systems.

2. Discussion of the Related Art

Approximately one-third of all food is grown in crops that require insect pollination. Most crops grown for their fruits (including vegetables such as squash, cucumber, tomato and eggplant), nuts, seeds, fiber (such as cotton), and hay (alfalfa grown to feed livestock), require pollination by insects. Pollinating insects also play a critical role in maintaining natural plant communities and ensuring production of seeds in most flowering plants. Pollination is the transfer of pollen from the male parts of a flower to the female parts of a flower of the same species, which results in fertilization of plant ovaries and the production of seeds. The main insect pollinators, by far, are bees, and while European honey bees (*Apis mellifera*) are the best known and widely managed pollinators, there are also hundreds of other species of bees, mostly solitary ground nesting species, that contribute some level of pollination services to crops and are very important in natural plant communities. The U.S. Department of Agriculture estimates that 80 percent of insect crop pollination is accomplished by honeybees.

Substantially all of this pollination needs is currently fulfilled by putting European honey bees in fields at the appropriate time for pollination. Pollination dependent on honey bees however is risky, expensive and inefficient. Bees are continuously at risk due to Colony Collapse Disorder, mites, disease, and many other catastrophic risks which are amplified by climate change. Bees are also expensive and are often the largest input cost in a crop, often higher than the cost of renting land and of irrigation. Bees can cost over $500 per acre for a one month rental. Bees also are inefficient pollinators. They pollinate by happenstance of carrying pollen on their feet which about ⅓ of the time makes contact with a flower's stigma to pollinate. Also, insect pollination requires farmers to dedicate up to half of a field to low production or non-producing pollinating varieties so that bees can easily move from the pollinator plant to the primary food crop plant without traveling too far. Additionally, bees only operate during the day when weather conditions are suitable and often crops do not pollinate because optimal weather conditions are not present.

Supplemental Mass Pollination (SMP) is the broadcast application of pollen to female flowers that are not isolated from airborne pollen. Methods include blowing pollen towards the female flowers. Devices used for SMP may include dusters, compressed-air sprayers, and motorized dusters operated from the ground or from a plane. SMP may also include electrostatic charging of the pollen grains prior to application of the pollen.

SUMMARY OF THE INVENTION

Several embodiments of the invention advantageously address the needs above as well as other needs by providing a vision-based pollination system comprising: a mobile apparatus; a storage tank coupled to the mobile apparatus and configured to hold a pollination liquid; a plurality of pollen applicators coupled to the mobile apparatus and configured to deliver liquid, the plurality of pollen applicators fluidly coupled to the storage tank by a conduit; and a plurality of pollination nodes, each pollination node operatively coupled to a plurality of pollen applicators, each pollination node including a vision system operatively coupled to a camera, each vision system comprising a processor, memory, and vision software, whereby each pollination node is configured to perform the steps of: repeatedly take digital photographs of a crop field as the vision-based pollination system traverses the crop field; identify a pollination location from the photographs; determine if at least one of the pollen applicators will be in a position to deliver the pollination liquid to the pollination location as the mobile apparatus traverses the field; upon determining that at least one of the pollen applicators will be in the position to deliver the liquid to the pollination location, select a selected pollen applicators in the position to deliver the pollination liquid to the pollination location; and operate the selected pollen applicators at the time when the selected pollen applicators is in the position to deliver the pollination liquid to the pollination location, whereby the pollination liquid is delivered to the pollination location.

In another embodiment, the invention can be characterized as a pollination liquid comprising sucrose, pollen, and deionized water, wherein the sucrose percentage by weight is within the range of 5%-20%, the pollen percentage by weight is within the range of 0.01%-1%, and the deionized water percentage by weight is within the range of 79%-94.99%.

BRIEF DESCRIPTION OF THE DRAWINGS

The above and other aspects, features and advantages of several embodiments of the present invention will be more apparent from the following more particular description thereof, presented in conjunction with the following drawings.

FIG. 1 is a perspective view of the vision-based pollination system in one embodiment of the present invention.

FIG. 2 is a side elevational view of the vision-based pollination system as shown in FIG. 1.

FIG. 3 is a rear elevational view of the vision-based pollination system as shown in FIG. 1.

Figure 4:
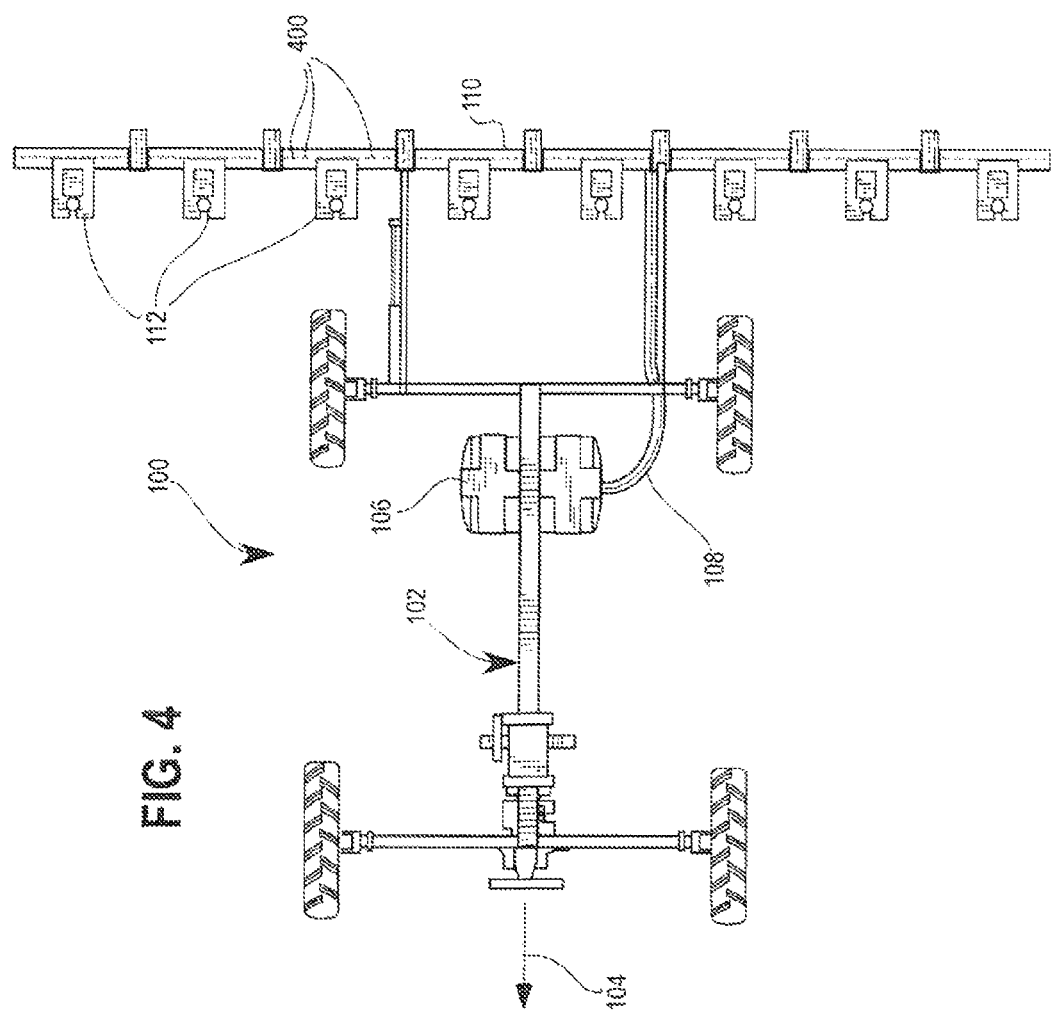
FIG. 4 is an underside view of the vision-based pollination system as shown in FIG. 1.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

DETAILED DESCRIPTION

The following description is not to be taken in a limiting sense, but is made merely for the purpose of describing the general principles of exemplary embodiments. The scope of the invention should be determined with reference to the claims.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art will recognize, however, that the invention can be practiced without one or more of the specific details, or with other methods, components, materials, and so forth. In other instances, well-known structures, materials, or operations are not shown or described in detail to avoid obscuring aspects of the invention.

Referring first to FIG. 1, a perspective view of a vision-based pollination system 100 is shown in one embodiment of the invention. Shown are a mobile apparatus 102, a direction of travel 104, a storage tank 106, a conduit 108, a support boom 110, and a plurality of pollination nodes 112.

The vision-based pollination system 100 includes the mobile apparatus 102, which is configured to provide the mobile platform for supporting the pollination elements and traversing a field, orchard, or other crop area to allow the vision-based pollination system 100 access to all plants or trees requiring pollination. The mobile apparatus 102 embodiment shown is a conventional agricultural tractor, but it will be appreciated by those of ordinary skill in the art that any suitable mobile conveyance may be used. In some embodiments, the mobile apparatus 102 may include a motorized structure mounted on a track. In other embodiments, the mobile apparatus 102 may be an aerial device, e.g. a drone. The mobile apparatus 102 may be configured for indoor or outdoor use. In some embodiments the mobile apparatus 102 is self-driving. In some embodiments the mobile apparatus 102 may include a GPS (Global Positioning System) receiver that may be programmed, for example, for specific coverage of certain pollination areas or to maintain a certain distance from the pollination system to the plants or trees. The mobile apparatus 102 is also structurally configured to provide support to the other elements of the vision-based pollination system 100, as described further below.

The mobile apparatus 102 as shown in FIG. 1 includes the support boom 110 coupled to the mobile apparatus 102. In the embodiment shown in FIG. 1, the support boom 110 is a straight tube shape coupled to a rear of the mobile apparatus 102. In some embodiments, as shown in FIG. 1, the support boom 110 is oriented substantially horizontally, with a support boom longitudinal axis generally perpendicular to the direction of travel 104 of the mobile apparatus 102. In some embodiments the support boom 110 may be movably coupled to the mobile apparatus 102, such that the support boom 110 may be raised or lowered or otherwise moved with respect to the mobile apparatus 102. The movable coupling may be operated manually or be a motorized or otherwise automatic coupling.

In some embodiments the support boom 110 may be configured in other shapes, such as a tube in an approximate U-shape with a lower central horizontal portion and two vertical side portions extending upward. Such a configuration could be used for tree pollination or other pollination where the flower to be pollinated may be located higher off the ground.

The storage tank 106 is coupled to and supported by the mobile apparatus 102. The storage tank 106 may be any configuration suitable for holding pollination liquid 700 and for fluidly coupling to a plurality of pollen applicators 400. In the embodiment shown in FIG. 1, the conduit 108 is used to fluidly couple the storage tank 106 to the pollen applicators 400. In some embodiments the storage tank 106 may be configured to hold a powdered pollen mixture. In other embodiments the storage tank 106 may be configured to hold the elements of the pollination liquid 700 separately and combine them in the storage tank 106 at certain time intervals. In some embodiments the time interval may be 20-60 minutes. The storage tank 106 may include additional tanks with additives that may be added to the storage tank 106 during pollination.

In the embodiment shown in FIG. 1, the plurality of pollen applicators 400 (not shown) are coupled to the underside of the support boom 110, and are described further below. The plurality of pollen applicators 400 are coupled to the storage tank 106 and configured to receive the pollination liquid 700 from the storage tank 106 and discharge the pollination liquid 700. As shown in FIG. 1, the conduit 108 is used to couple the storage tank 106 to the pollen applicators 400. The conduit 108 in some embodiments is coupled at the end distal to the storage tank 106 to a manifold that run through and is supported by the support boom 110. The pollen applicators 400 are then coupled to the manifold. In some embodiments the pollination liquid 700 is pressurized such that the pollen applicators 400 may discharge a spray upon opening a valve of the pollen applicator 400. In some embodiments, the pressurization of the pollination liquid 700 may be varied so that the pollination liquid 700 may be applied at varying distances from the pollen applicator 400. In some embodiments, the pollen applicators 400 may be configured to vary a direction of application, e.g. by configuring the pollen applicator 400 for rotation.

In accordance with some variations, the pollination liquid 700 may be electrostatically charged (such as by using a Wimshurst generator, pelletron, Van de Graff generator, variants and combinations of these, and/or through the inherent electrostatic charge resultant from the friction between the flowing pollination liquid 700 and the manifold and pollen applicators 400), so as to impart an electrostatic charge to the pollination liquid 700 relative to the target stigma in the flower. Advantageously, the electrostatically charged pollination liquid 700 is thereby attracted to the target stigma in the flower as a result of this relative electrostatic charge, thereby further facilitating deposition of the pollination liquid 700 onto the target stigma in the flower and adherence of the pollination liquid 700 to the target stigma in the flower.

The plurality of pollination nodes 112 are coupled to the support boom 110. In other embodiments the pollination nodes 112 may be coupled directly to the mobile apparatus 102. While a plurality of pollination nodes 112 are shown spaced generally regularly along the longitudinal axis of the support boom 110, it will be appreciated that the vision-based pollination system 100 may include only a single pollination node 112. Each pollination node 112 is operatively coupled to at least one pollen applicator 400 (not shown), i.e. the pollination nodes 112 are configured to control when the pollen applicator 400 discharges the pollination liquid 700. The pollination nodes 112 are also configured to use vision system capabilities to locate flowers and determine when to discharge the pollination liquid 700 in order to optimize the likelihood of flower pollination, as is described further below.

In the present embodiment, the pollination liquid 700 is comprised of 89.9% deionized water, 10% sucrose, and 0.1% pollen by weight. In some embodiments the percentage of pollen may vary between 0.01% and 1%. In some embodiments the percentage of sucrose may vary between 5% and 20%.

Referring again to FIG. 1, the exemplary vision-based pollination system 100 is shown in one embodiment of the present invention. The pollination nodes 112, utilizing vision systems, can achieve a much higher rate of pollination by precisely targeting the stigma in the flower. Farming practices would be much more efficient with mechanical vision-based pollination because the pollinator varieties can be located off-site in less desirable agricultural land and the pollen harvested and moved to the site of the desired crop requiring pollination. As it would not be necessary for farmers to dedicate up to half of a field to low production or non-producing pollinating varieties so that bees can easily move from the pollinator plant to the primary food crop plant without traveling too far, farmers using the vision-based pollination system 100 would be able to plant 100% of their fields to the desired crop. In addition, the vision-based pollination system 100 can be used 24 hours a day under any weather conditions, increasing the ability to capture time sensitive blooms regardless of weather conditions.

The vision-based pollination system 100 may be configured for use in applications of differing scope. For example, the mobile apparatus 102 may be configured for use in fields of lower-height plants, or the vision-based pollination system 100 may be configured for use in tree orchards. The pollen applicators 400 may be configured for vertical movement as well as the horizontal movement provided by the mobile apparatus 102. The pollen applicators 400 may be configured to change the direction of delivery of the pollination liquid 700.

Referring next to FIGS. 2 and 3, a side elevational view and a rear elevational view of the vision-based pollination system 100 of FIG. 1 are respectively shown. Shown are the mobile apparatus 102, the direction of travel 104, the storage tank 106, the plurality of pollination nodes 112, the storage tank 106, and the conduit 108. As previously described, the mobile apparatus 102 is configured to move around the area to be pollinated and provide support for the various pollination elements previously described.

Referring next to FIG. 4, an underside view of the vision-based pollination system 100 of FIG. 1 is shown. Shown are the mobile apparatus 102, the storage tank 106, the conduit 108, the support boom 110, the pollination nodes 112, and the plurality of pollen applicators 400.

In FIG. 4, the pollen applicators 400 are shown coupled to an underside of the support boom 110. In the embodiment shown, the pollen applicators 400 are arranged in a single row extending substantially the length of the support boom 110. In the embodiment shown, the conduit 108 extends from the storage tank 106 to the support boom 110, where the conduit 108 passes through an opening in the support boom 110 and into the interior of the support boom 110, where the conduit 108 is fluidly coupled to a tubular manifold 500, the manifold 500 in turn coupled to the plurality of pollen applicators 400. In other embodiments the manifold 500 may run externally along the support boom 110.

Each pollen applicator 400 is coupled to one of the plurality of pollination nodes 112 for operation of the pollen applicator 400 by the pollination node 112, as described further below. In one embodiment, each pollen applicator 400 includes an electronic trigger which is operated by the pollination node 112. In one embodiment, the pollen applicators 400 are spray nozzles. The pollen applicators 400 may be configured to deliver the pollination liquid 700 in a specific direction, such as downward, or may be rotatable for delivery in different directions. The pollen applicators 400 in some embodiments are manually movable, or in other embodiments the may be configured to be moved during the pollination process by the pollination node 112. The pollen applicators 400 may be configured to provide a spray distance based on the pressure of the pollination liquid 700 in the manifold 500, i.e. provide a simple valve opening, or the pollen applicators 400 may be configured to provide varying pressures of spray resulting in varying spray distances. The pollen applicators 400 may be configured to provide a stream of pollination liquid 700 to the target, or may provide varying types of pollination liquid spray. In some embodiments the pollen applicators 400 or other elements of the system are configured to induce a positive or negative electrostatic charge on the pollination liquid 700 in order to enhance efficiency.

Referring next to FIG. 5, a perspective view of a portion of the vision-based pollination system 100 including one of the plurality of pollination nodes 112 is shown in accordance with one embodiment of the invention. Shown are the support boom 110, the manifold 500, the plurality of pollen applicators 400, the pollination node 112, a node support 502, a vision system enclosure 504, the direction of travel 104, and a camera 506.

The pollination node 112 includes the vision system enclosure 504, which encloses vision system elements of a vision system 600 as described further below in FIG. 6. The pollination node 112 also includes the camera 506 and the node support 502. The vision system enclosure 504 and the camera 506 are coupled to and supported by the node support 502, which is in turn supportively coupled to the support boom 110. In the embodiment shown, the node support 502 is cantilevered from the support boom 110. In other embodiments the vision system elements and the camera 506 may be coupled directly to the support boom 110 or the mobile apparatus 102, without the additional node support 502. As shown in FIG. 5, there is a distance between the camera 506 location and each pollen applicator 400. The vision system 600 includes the data for the distances from the camera 506 location to the location of each pollen applicator 400. As the vision-based pollination system 100 moves in the direction of travel 104, the camera 506 photographs an area before the pollen applicators 400 pass over the same area. This allows the vision system 600 to analyze the pollination locations of the area and determine which pollen applicator or applicators 400 to operate before the pollen applicators 400 pass over the photographed area.

As previously described, the pollen applicators 400 are coupled to the underside of the support boom 110. In the embodiment shown, a portion of the line of pollen applicators 400 is operated by the vision system 600. In the embodiment shown in FIG. 5, the segment of pollen applicators 400 coupled to the pollination node 112 shown in FIG. 6 is centered on the pollination node 112. Forty-five pollen applicators 400 are shown coupled to the pollination node 112 of FIG. 5, but it will be understood that more or fewer pollen applicators 400 may be coupled to the pollination node 112. In one embodiment, a size of the pollination node 112 permits a maximum of 72 pollen applicators 400 comprising ¼" spray nozzles to be coupled to the pollination node 112. In other embodiments of the size of the pollination node 112 and size of the pollen applicators 400, more or fewer pollen applicators 400 may be coupled to the pollination node 112.

Figure 5:
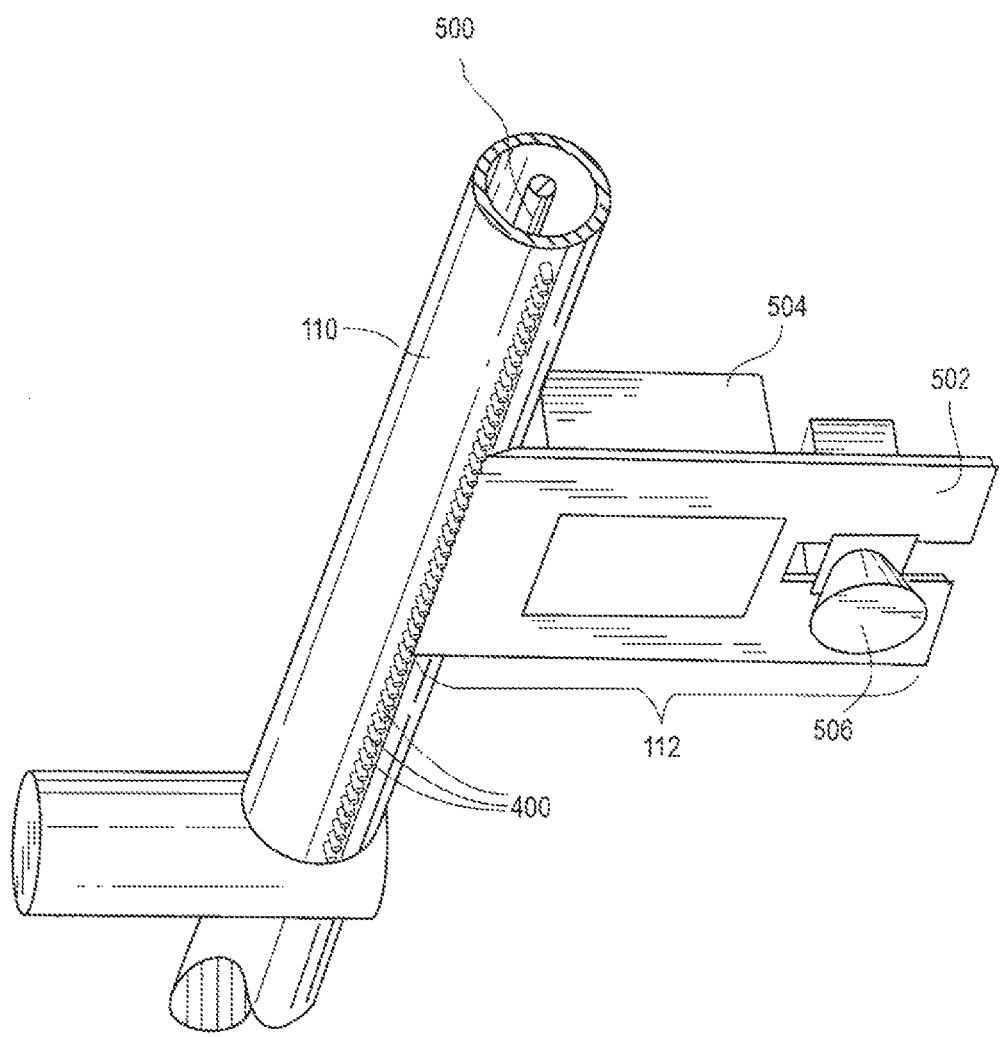
FIG. 5 is a perspective view of a portion of the vision-based pollination system, including one of the plurality of pollination nodes, in accordance with the vision-based pollination system of FIG. 1.
Figure 6:
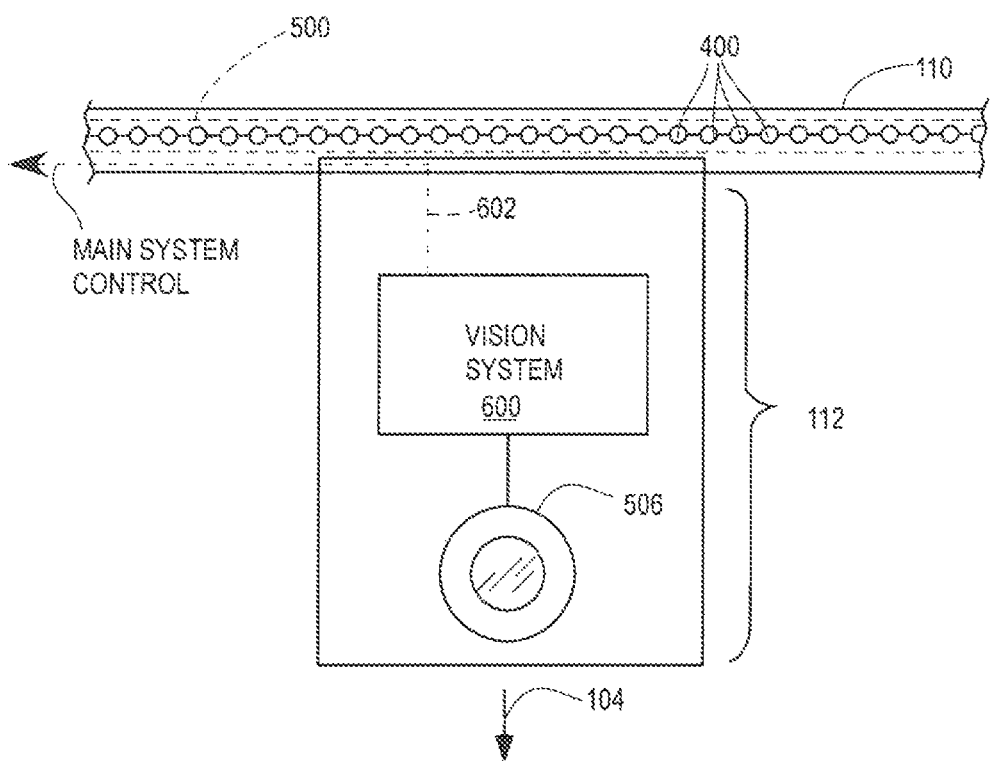
FIG. 6 is a schematic diagram of the pollination node and associated pollen applicators is shown, in accordance with the vision-based pollination system of FIG. 1.

The camera 506 as shown in FIG. 5 is oriented such that a camera lens is facing downward. In other embodiments the camera 506 may be oriented at a different angle, or may be configured to allow the angle of the camera 506 to change during operation of the vision-based pollination system 100.

Referring next to FIG. 6, a schematic diagram of the pollination node 112 and associated pollen applicators 400 is shown. Shown are the camera 506, the pollen applicators 400, the vision system 600, the support boom 110, the manifold 500, the pollen applicators 400 and a main system control connection 602.

As previously shown, the pollination node 112 includes the vision system 600 and the camera 506 coupled to the vision system 600. The vision system 600 includes a computing system configured to receive the photos taken from the camera 506, analyze the photos to determine a pollination location (e.g. a flower or a portion of a flower such as a stigma of a flower) to be pollinated, and activate the pollen applicator 400 at an appropriate time to deliver the pollination liquid 700 to the pollination location as the vision-based pollination system 100 travels over the area.

In some embodiments the computing system includes a processor, vision software configured to run on the processor, and non-transitory memory as required to store the vision software and perform required processor and software operations. The vision software is configured to perform the various computations and analyses required to perform the above-mentioned function. The vision software operates the camera 506, determining time and frequency of photos, and also receives the photos and stores them in the vision system 600. In some embodiments the vision software can delete older photos no longer required by the software (e.g. from a previous field). As the vision software receives the photos taken as the vision-based pollination system 100 advances, the vision software identifies flowers in the photos to be pollinated. The criteria for determining which flowers are to be pollinated may be determined by inputs previously set by a user, or by an algorithm of the vision software. Criteria for selecting the flower may include visibility under visible light and flower shape. The vision software also compares the current photo to previous photos and determines a current speed and direction of the vision-based pollination system 100. Based on the speed and direction determination, the vision software determines which pollen applicator 400 will be in the best position for delivering the pollination liquid 700 to the pollination location, and the application time when that pollen applicator 400 will be in the best position to spray the pollination location. When the application time is reached, the vision software, which through the vision system 600 is in operable communication with the pollen applicators 400, activates the selected pollen applicators 400 to deliver the pollination liquid 700 to the pollination locations, e.g. the stigma of flowers.

In some embodiments, each vision system 600 includes a display and a user input (e.g. keyboard or touchscreen). In other embodiments, the vision system 600 may be configured to be connected to an external display and input system. In other embodiments, the vision system 600 of each pollination node 112 is communicatively coupled to a central computing system, as shown by the optional main system control connection 602. The main system control connection 602 may be used to operate the pollination nodes 112 and/or provide user input to change system parameters.

In some embodiments the vision software may include proprietary image processing software as a separate module in communication with the vision software.

The camera 506 may be a visual light camera or in some embodiments may be configured to capture ultraviolet light. The software may be configured to analyze the photographs based on the ultraviolet parameters.

In some embodiments the vision system 600 also controls the pressure of the pollination liquid 700 during application/delivery.

In some embodiments, each photo is of a 3'×3' area, although different photo area sizes may be used, based on spacing of the pollination nodes 112, speed of the vision-based pollination system 100, distance of the support boom 110 from the flowers, or other variables.

In some embodiments additional devices may be coupled to the vision system 600. In one embodiment the device is an accelerometer providing acceleration data to the vision system 600, which is then configured to analyze the accelerometer data and use it to determine the current movements and predict future movements of the vision-based pollination system 100.

Figure 7:
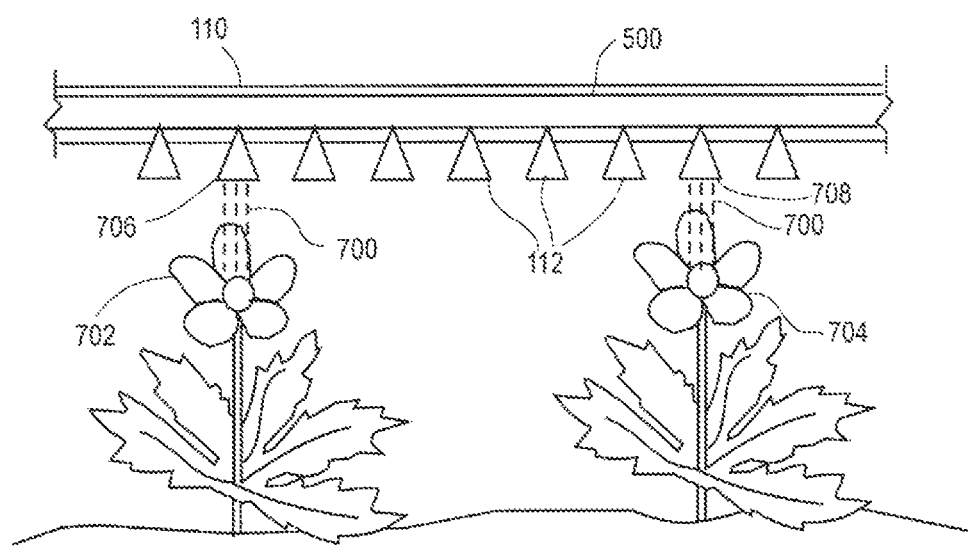
FIG. 7 is a front elevational view of a portion of the support boom is shown with the vision-based pollination system in operation.

Referring next to FIG. 7, a front elevational view of a portion of the support boom 110 is shown with the vision-based pollination system 100 in operation. Shown are the support boom 110, the manifold 500, the plurality of pollen applicators 400, the pollination liquid 700, a first flower 702, a second flower 704, a first spray nozzle 706, and a second spray nozzle 708.

A portion of the vision-based pollination system 100 is shown in operation in FIG. 7. The support boom 110 is moving across the crop field in a direction perpendicular to the plane of the page. In the embodiment shown, the pollen applicators 400 are spray nozzles with a downward spray direction. The vision system 600 has previously photographed the field area including the first flower 702 and second flower 704, and has determined that as the vision-based pollination system 100 traverses the field, the first spray nozzle 706 will be positioned to pollinate the first flower 702, and the second spray nozzle 708 will be in position to pollinate the second flower 704. As the support boom 110 with the pollen applicators 400 passes over the first flower 702 and the second flower 704, the pollination node 112 operating the first spray nozzle 706 and the second spray nozzle 708 (pollination node 112 not shown) activates the first spray nozzle 706 at the appropriate time to deliver pollination liquid 700 to the first flower 702, and also activates the second spray nozzle 708 at the appropriate time to deliver pollination liquid 700 to the second flower 704. As shown in FIG. 7, the first spray nozzle 706 and the second spray nozzle 708 are activated at the same time, but it will be understood that the spray nozzles 706, 708 may be activated at different times depending on the flower locations.

Figure 8:
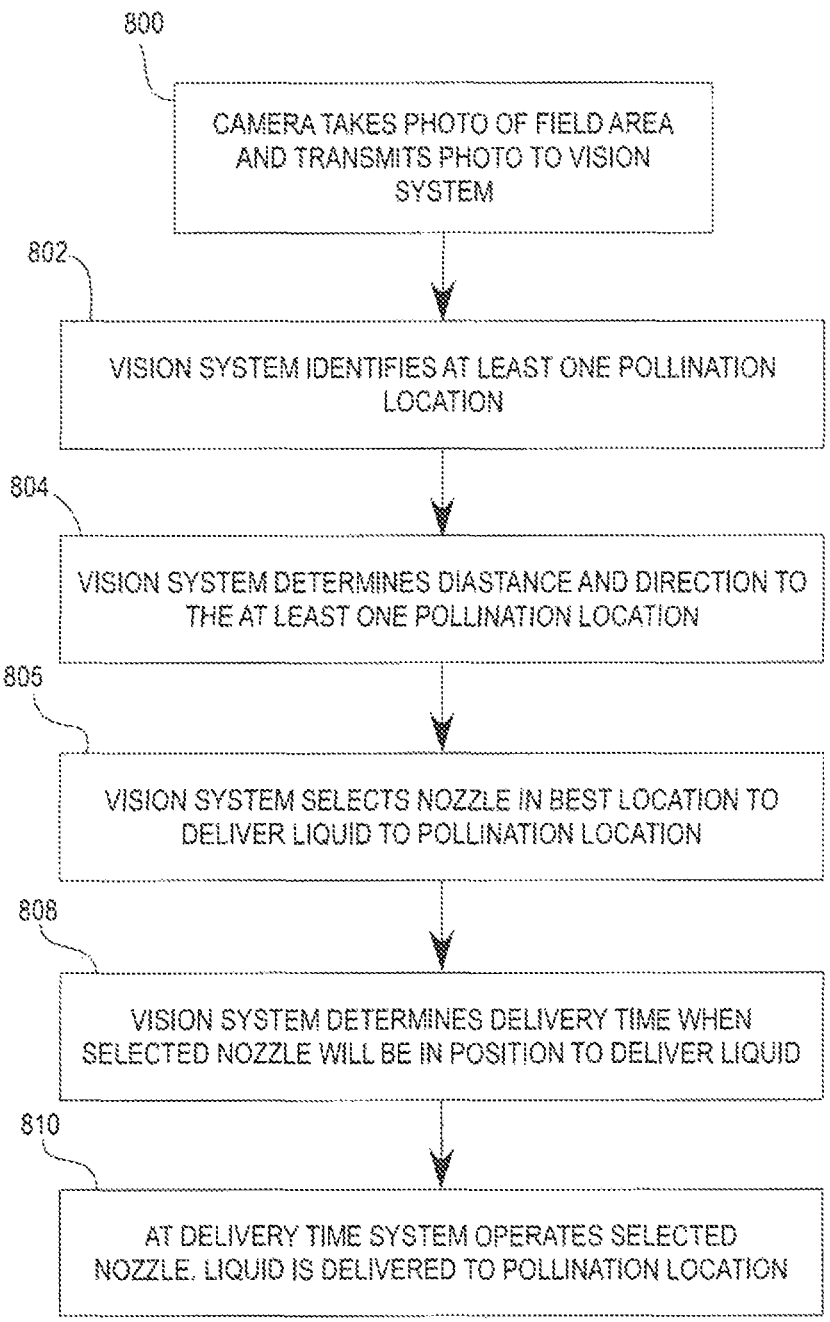
FIG. 8 is a flowchart of the operational process of the vision-based pollination system in one embodiment of the present invention.

Referring next to FIG. 8, a flowchart of the operational process of the vision-based pollination system 100 is shown. Shown are a photo step 800, a determine pollination location step 802, a distance determination step 804, a nozzle selection step 806, an estimate delivery time step 808, and a pollination step 810.

In the first photo step 800, as the vision-based pollination system 100 is traversing the field, the vision system 600 directs the camera 506 to take repeated photographs of the field area. The camera 506 sends the photographs to the vision system 600 for analysis. The photographs may be taken at a set timing interval, or the timing interval may be variable. In one example, the timing interval varies depending on the speed of the vision-based pollination system 100.

In the next step, the determine pollination location step 802, the vision system 600 analyzes the photographs and determines at least one pollination location that will be in a position to be sprayed by one of the pollen applicators 400 as the vision-based pollination system 100 continues to traverse the field. As previously noted, various criteria may be used to determine the locations chosen for pollination. The process then proceeds to the distance determination step 804.

In the distance determination step 804, the vision system 600 determines the distance and direction to the pollination location (or pollination locations, if multiple pollination locations are determined). In some embodiments, the vision system 600 is configured to assign an x, y coordinate location to the pollination location relative to an x,y coordinate location of the camera 506 at the time the photograph was taken.

Next, in the nozzle selection step 806, for each identified pollination location the vision system 600 selects the pollen applicator 400 that will be in the optimal location to apply the pollination liquid 700 to the pollination location. In one embodiment, the current speed and direction of the vision-based pollination system 100 is determined by comparing consecutive photographs, and the speed and direction are used to calculate the trajectory of the pollen applicators 400 with respect to the pollination location. In other embodiments, additional devices, such as the accelerometer, a GPS device, and/or a compass may be used to anticipate the movement trajectory of the pollen applicators 400. In other embodiments, the vision system 600 may receive a future trajectory from the central control device of the vision-based pollination system 100 and use that to anticipate the location of the pollen applicators 400. The process then proceeds to the estimate delivery time step 808.

During the estimate delivery time step 808, using the vision-based pollination system 100 trajectory information as mentioned in the previous nozzle selection step 806, the vision system 600 determines, for each selected pollen applicator 400, a delivery time when the selected pollen applicator 400 will be in the optimal position to deliver the pollination liquid 700 to the pollination location.

In the final step, the pollination step 810, at the determined delivery time the selected pollen applicator 400 is activated and the pollination liquid 700 is applied to the pollination location (e.g. the stigma of the flower).

The process then repeats, with the camera 506 taking photographs, the vision system 600 determining pollination locations, and activating the selected pollen applicators 400 at the appropriate delivery times to apply the pollination liquid 700 to the pollination locations.

In some embodiments the vision-based pollination system 100 can be configured to move in three dimensions (for example, when applying the pollination liquid 700 to a tree), wherein the vision system 600 would be modified to track the pollination locations and the movement of the vision-based pollination system 100 in three dimensions.

Figure 9:
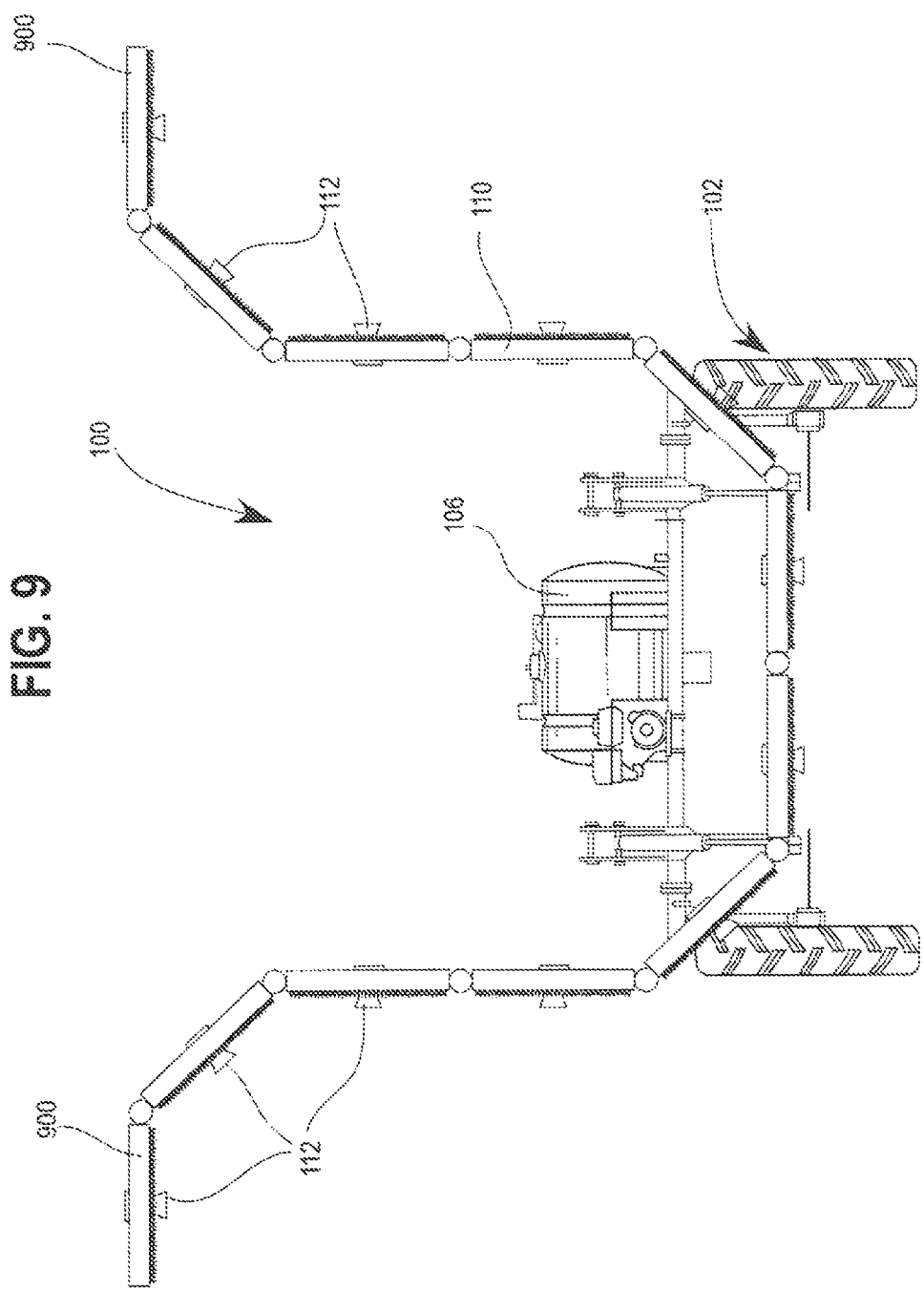
FIG. 9 is a rear elevational view of the vision-based pollination system in another embodiment of the present invention.

Referring last to FIG. 9, a rear elevational view of the vision-based pollination system 100 is shown in a tree-pollinating embodiment of the present invention. Shown are the mobile apparatus 102, the storage tank 106, the support boom 110, the plurality of pollination nodes 112, and two support boom flanges 900.

As shown in FIG. 9, the support boom 110 had been modified from the generally linear horizontal configuration previously shown in FIGS. 1-4. Each end portion of the support boom 110 is configured to extend in an upward direction as well as extending outwardly past the extent of the mobile apparatus 102. In the exemplary configuration shown in FIG. 9, the support boom is a generally U-shaped configuration, with additional flange portions 900 of the support boom 110 extending in a horizontal direction away from the mobile apparatus 102.

The pollination nodes 112 are arranged at regular intervals on the support boom, as previously shown. The pollen applicators 400 (not shown) are also arranged on the support boom 110 as previously shown, i.e. the pollen applicators 400 in the present configuration can reach a variety of vertical locations as well as horizontal locations.

The vision-based pollination system 100 shown in FIG. 9 is configured to pollinate trees and other plants where the flowers are not located proximate to the ground. It will be apparent to those of ordinary skill in the art that other vertical configurations of the support boom 110 may be desirable depending on the size, width, and/or other physical characteristics of the plant or tree to be pollinated.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

While the invention herein disclosed has been described by means of specific embodiments, examples and applications thereof, numerous modifications and variations could be made thereto by those skilled in the art without departing from the scope of the invention set forth in the claims.

What is claimed is:

1. A vision-based pollination system comprising:
- a mobile apparatus;
- a storage tank coupled to the mobile apparatus and configured to hold a pollination liquid;
- at least one pollen applicator segment, each pollen applicator segment including a plurality of pollen applicators wherein each pollen applicator is coupled to the mobile apparatus and configured to deliver liquid, each pollen applicator fluidly coupled to the storage tank by a conduit; and
- at least one pollination node, each pollination node operatively coupled to one pollen applicator segment, each pollination node including a vision system operatively coupled to a camera, each vision system comprising a processor, memory, and vision software, whereby each pollination node operatively controls pollen applicators in one pollen applicator group, whereby each pollination node is configured to perform the steps of:
  - repeatedly take digital photographs of a crop field as the vision-based pollination system traverses the crop field;
  - identify a pollination location from the photographs;
  - determine if at least one of the pollen applicators of the pollen applicator segment will be in a position to deliver the pollination liquid to the pollination location as the mobile apparatus traverses the crop field;
  - upon determining that at least one of the pollen applicators of the pollen applicator segment will be in the position to deliver the liquid to the pollination location, select the at least one pollen applicator in the position to deliver the pollination liquid to the pollination location; and
  - operate each selected at least one pollen applicator at a time when each selected at least one pollen applicator is in the position to deliver the pollination liquid to the pollination location, whereby the pollination liquid is delivered to the pollination location.

2. The vision-based pollination system of claim 1, further comprising a support boom coupled to a rear of the mobile apparatus and supporting the pollination nodes and the pollen applicators.

3. The vision-based pollination system of claim 2, wherein the support boom includes a tube portion oriented substantially horizontally and with a support boom longitudinal axis generally perpendicular to a direction of travel of the mobile apparatus.

4. The vision-based pollination system of claim 3, wherein the support boom further includes a vertical arm at each end of a central horizontal portion of the support boom, whereby a U-shaped support boom is formed.

5. The vision-based pollination system of claim 2, wherein the support boom is a tube shape, wherein the conduit includes a manifold running through the support boom.

6. The vision-based pollination system of claim 2, wherein the support boom is movably coupled to the mobile apparatus such that the support boom may be moved with respect to the mobile apparatus.

7. The vision-based pollination system of claim 1, wherein the mobile apparatus is a wheeled apparatus.

8. The vision-based pollination system of claim 7, wherein the mobile apparatus is a tractor.

9. The vision-based pollination system of claim 1, wherein the mobile apparatus is mounted on a track.

10. The vision-based pollination system of claim 1, wherein the mobile apparatus is suspended above the crop field.

11. The vision-based pollination system of claim 1, wherein the mobile apparatus includes a GPS system.

12. The vision-based pollination system of claim 1, wherein the pollination location is a stigma of a flower.

13. The vision-based pollination system of claim 1, wherein the vision-based pollination system is configured to pressurize the pollination liquid.

14. The vision-based pollination system of claim 13, wherein the vision-based pollination system is configured to deliver the pollination liquid at varying distances from the pollen applicators.

15. The vision-based pollination system of claim 1, further comprising the pollination liquid stored in the storage tank.

16. The vision-based pollination system of claim 15, wherein the pollination liquid comprises sucrose, pollen, and deionized water.

17. The vision-based pollination system of claim 16, wherein a percentage of pollen by weight is within the range of 0.01% and 1%.

18. The vision-based pollination system of claim 16, wherein a percentage of deionized water by weight is within the range of 79%-94.99%.

19. The vision-based pollination system of claim 16, wherein a sucrose percentage by weight is within the range of 5%-20%.

20. The vision-based pollination system of claim 1, wherein the pollination location is a stigma of a flower visible in at least one of the photographs.

21. The vision-based pollination system of claim 1, wherein the camera is configured to detect ultraviolet light.

22. The vision-based pollination system of claim 21, wherein the pollination location is determined based at least on crop characteristics viewable in ultraviolet light.

* * * * *